US00PP09777P

United States Patent [19]

Meilland

[11] Patent Number: Plant 9,777

[45] Date of Patent: Jan. 7, 1997

[54] FLORIBUNDA ROSE PLANT NAMED 'MEIPOPUL'

[75] Inventor: Alain A. Meilland, Antibes, France

[73] Assignee: The Conard-Pyle Company, West Grove, Pa.

[21] Appl. No.: 555,726

[22] Filed: Nov. 9, 1995

[51] Int. Cl.[6] ..... A01H 5/00

[52] U.S. Cl. ..... Plt./22

[58] Field of Search ..... Plt./22, 25, 26, Plt./27

[56] References Cited

U.S. PATENT DOCUMENTS

P.P. 1,608 6/1957 Shepherd ..... Plt./27

P.P. 2,209 1/1963 LeGrice ..... Plt./27

*Primary Examiner*—Howard J. Locker

*Attorney, Agent, or Firm*—Burns, Doane, Swecker & Mathis, L.L.P.

[57] ABSTRACT

A new and distinct variety of Floribunda rose plant is provided which abundantly forms attractive single scarlet red blossoms on a substantially continuous basis. The plant exhibits a bushy growth habit. Attractive very dense semi-glossy foliage is formed. The new variety is particularly well suited for growing as ornamentation in the landscape. Very good disease resistance also is exhibited.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) was the product of the cross of the 'Korimo' variety (non-patented in the United States) and the 'Lenwich' variety (non-patented in the United States). The male parent (i.e., the pollen parent) of the new variety was the product of the cross of the 'Temple Bells' variety (non-patented in the United States) and the 'Moorcap' variety (also known as 'Red Cascade', U.S. Plant Pat. No. 3,962). The parentage of the new variety can be summarized as follows:

('Korimo'×'Lenwich') ×('Temple Bells'×'Moorcap').

The seeds resulting from the above pollination were sown and 78 small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive single scarlet red blossoms on a substantially continuous basis,
(b) exhibits a bushy growth habit,
(c) forms attractive very dense semi-glossy vegetation, and
(d) is particularly well suited for growing as ornamentation in the landscape.

The new variety has undergone asexual propagation by a number of routes in France, including budding, grafting, and cuttage. The characteristics of the new variety have been found to be strictly transmissible by such asexual propagation from one generation to another in France.

The new variety has been named the 'Meipopul' variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and were observed during June while growing on their own roots outdoors at Le Cannet des Maures, Var, France.

FIG. 1 — illustrates a specimen of a young shoot;

FIG. 2 — illustrates specimens of floral buds before the opening of the sepals;

FIG. 3 — illustrates specimens of floral buds at the opening of the sepals;

FIG. 4 — illustrates specimens of two floral buds at the opening of the petals;

FIG. 5 — illustrates specimens of two petals;

FIG. 6 — illustrates a specimen of an open flower—plan view— obverse;

FIG. 7 — illustrates a specimen of an open flower—plan view— reverse;

FIG. 8 — illustrates a specimen of a fully open flower—plan view—obverse;

FIG. 9 — illustrates a specimen of a fully open flower—plan view— reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of two leaves with three leaflets with the upper surface at the right and under surface at the left;

FIG. 15 — illustrates specimens of two leaves with seven leaflets with the upper surface at the top and the under surface at the bottom; and FIG. 16 — illustrates specimens of two leaves with five leaflets with the upper surface at the right and the under surface at the left.

DETAILED DESCRIPTION

Figures 1, 2, 3, 4, 5, 6, 7, 8, 9, 10, 11, 12, 13, 14, 15, 16:
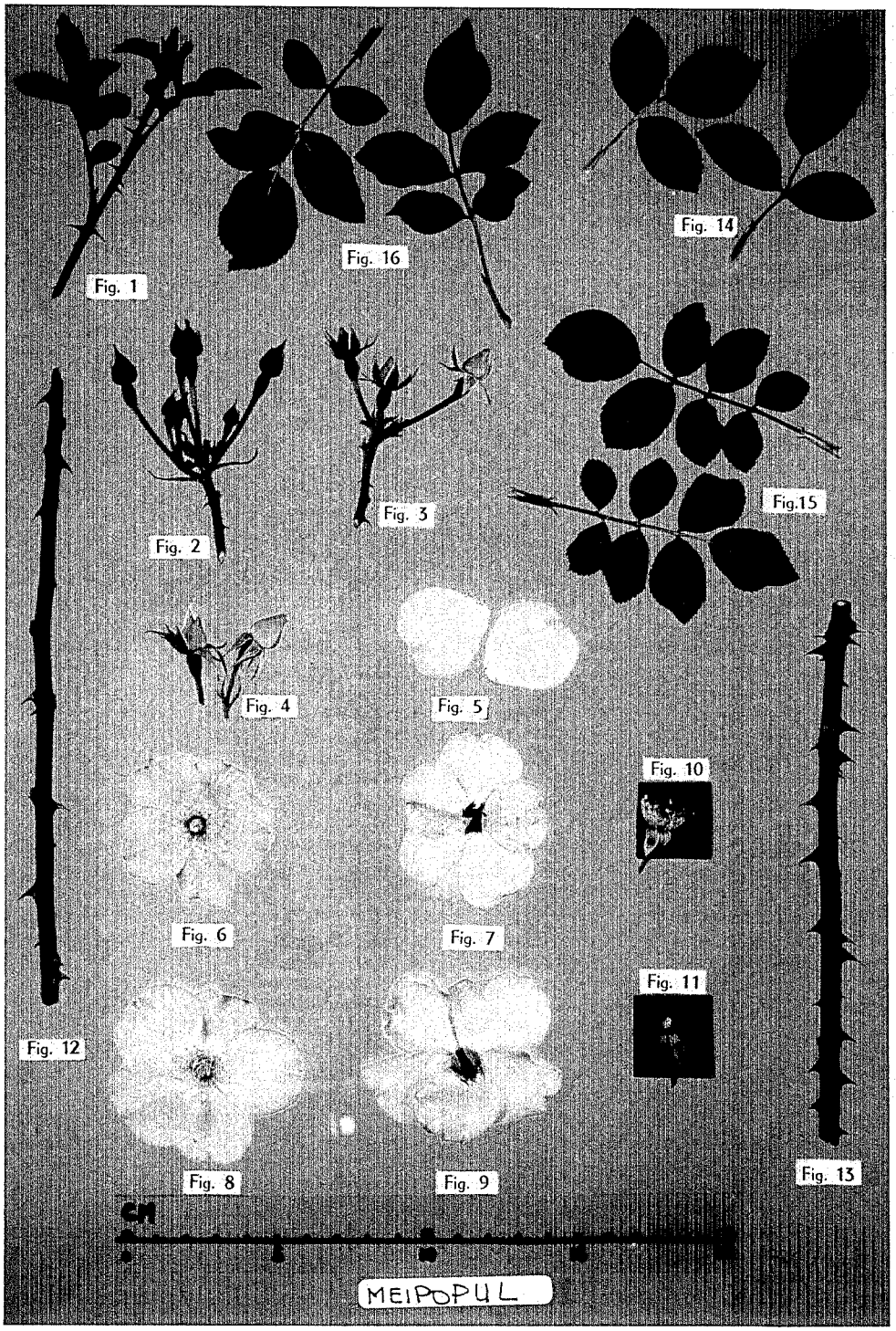

The chart used in the identification of the colors is that of The Royal Horticultural Society (R.H.S. Colour Chart). The terminology which preceeds reference to the chart has been added to indicate the corresponding color in more common terms. The description is based on two year old specimens of the new variety during May while growing on their own roots outdoors at Le Cannet des Maures, Var, France.

Class: Floribunda.

Plant:

*Height.*—Plants commonly achieve a height of approximately 70 to 90 cm. at the end of the growing season.

*Habit.*—Bushy.

Branches:

*Color.*—Young Stems: reddish brown. Adult wood: light green, Yellow-Green Group 146C.

*Thorns.*—Size: small to medium. Quantity: numerous. Color: reddish on young wood and pinkish on adult wood.

Leaves:

*Stipules.*—Adnate, pectinate, wide and relatively large.

*Petioles.*—Upper surface: striped reddish on young foliage and medium green and more or less glandular on adult wood. Under surface: light green with numerous small thorns.

*Leaflets.*—Number: 3, 5, and 7 (most often). Shape: elliptic. Serration: single and regular (as illustrated). Texture: consistent. General appearance: very dense, and semi-glossy (as illustrated). Color (young foliage): upper surface: reddish brown in coloration under surface: reddish brown in coloration Color (adult foliage): upper surface: dark green, Green Group 137A. under surface: light green, Green Group 137C.

Inflorescence:

*Number of flowers.*—Commonly approximately 1 to 15 flowers per stem.

*Peduncle.*—Light green and glandular, and approximately 2.5 to 3 cm. in length on average.

*Sepals.*—Upper surface: tomentose, and greenish in coloration. Under surface: greenish and more or less suffused with reddish coloration with more or less apendiculate edges.

*Buds.*—Shape: conical. Length: approximately 1.5 cm. on average. Size: small. Color upon opening: upper surface: Signal Red, Red Group 43A. under surface: Delft Pink, Red Group 46D, and widely suffused with Turkey Red, Red Group 46C.

*Flower.*—Shape: cup-shaped. Diameter: approximately 6 cm. on average. Type: single. Color: (when opening begins): upper surface: bright Scarlet, Red Group 43C. under surface: light Neyron Rose, Red-Purple 58C. Color: (when blooming): upper surface: bright Scarlet, Red Group 43C. under surface: light Neyron Rose, Red-Purple 58C. Color (at end of opening): upper surface: bright Scarlet, Red Group 43C. under surface: light Neyron Rose, Red-Purple Group 58C. Fragrance: absent. Petal drop: good. Petal form: rounded and often with a tip (as illustrated). Petal number: approximately 5 on average (as illustrated). Stamen number: approximately 98 to 102 on average. Anthers: ochre in coloration. Filaments: ochre in coloration. Pistils: approximately 23 on average. Stigmas: ochre in coloration. Styles: yellowish in coloration. Receptacle: light green, smooth, and in longitudinal section in the shape of a narrow pear.

Development:

*Vegetation.*—Strong.

*Blooming.*—Precocious, abundant and substantially continuous.

*Aptitude to bear fruit.*—Good.

*Resistance to diseases.*—Very good.

I claim:

1. A new and distinct variety of Floribunda rose plant characterized by the following combination of characteristics:

(a) forms in abundance attractive single scarlet red blossoms on a substantially continuous basis,
(b) exhibits a bushy growth habit,
(c) forms attractive very dense semi-glossy vegetation, and
(d) is particularly well suited for growing as ornamentation in the landscape;

substantially as herein shown and described.

* * * * *

CM
MEIPOPUL